United States Patent [19]

Gönner

[11] 3,954,291

[45] May 4, 1976

[54] REUSABLE SEALED COUPLING FOR GLASS TUBES

[75] Inventor: Winfried Karl Gönner, Uberlingen, Germany

[73] Assignee: Bodenseewerk Perkin-Elmer & Co. GmbH, Uberlingen, Germany

[22] Filed: Jan. 14, 1974

[21] Appl. No.: 432,805

[30] Foreign Application Priority Data

Jan. 13, 1973 Germany............................ 2301749
Sept. 25, 1973 Germany............................ 2348071

[52] U.S. Cl................................. 285/341; 285/356
[51] Int. Cl.² .................... F16L 17/00; F16L 19/06; F16L 19/08; F16L 21/02
[58] Field of Search ........... 285/341, 342, 343, 238, 285/356, 357, 351, DIG. 12

[56] References Cited

UNITED STATES PATENTS

| | | | |
|---|---|---|---|
| 2,190,419 | 2/1940 | Evarts............................ | 285/356 X |
| 2,308,757 | 1/1943 | Hulsberg........................ | 285/356 X |
| 3,756,632 | 9/1973 | Riggs et al...................... | 285/356 X |

FOREIGN PATENTS OR APPLICATIONS 1,027,172    2/1953    France.................................. 285/341

Primary Examiner—Werner H. Schroeder
Assistant Examiner—Wayne L. Shedd
Attorney, Agent, or Firm—S. A. Giarratana; F. L. Masselle; J. K. Conant

[57] ABSTRACT

In a connecting device for connecting chromatographic separating columns of glass to terminal fittings on a chromatographic apparatus, each end of the column is surrounded by a metallic sleeve. A sleeve made of synthetic plastic material, which is of substantially stable shape at least up to a temperature of 350°C. even if subjected to pressure, is interposed between said end and said metallic sleeve. A preferred material is polyimide. The plastic sleeve has at least one conical end face and is held in sealing engagement with the end of the separating column, on one hand, and with the metallic sleeve, on the other hand, by a sleeve shaped thrust member, which is axially movable relative to the metallic sleeve to exert an axial force on said plastic sleeve. A radial sealing force is exerted on the synthetic plastic sleeve through its conical end face by an abutting complementary conical surface. Conventional connecting means for gas-tightly and detachably connecting the ends of the column to the terminal fittings of the apparatus are provided on the metallic sleeve. In another embodiment the plastic sleeve is made of polytetrafluoroethylene, and the sleeve is held in sealing engagement with the metallic sleeve and the end of the separating column at an adjustable minimum axial pressure. This pressure is exerted through a sleeve-shaped thrust member by a compressed spring.

4 Claims, 2 Drawing Figures

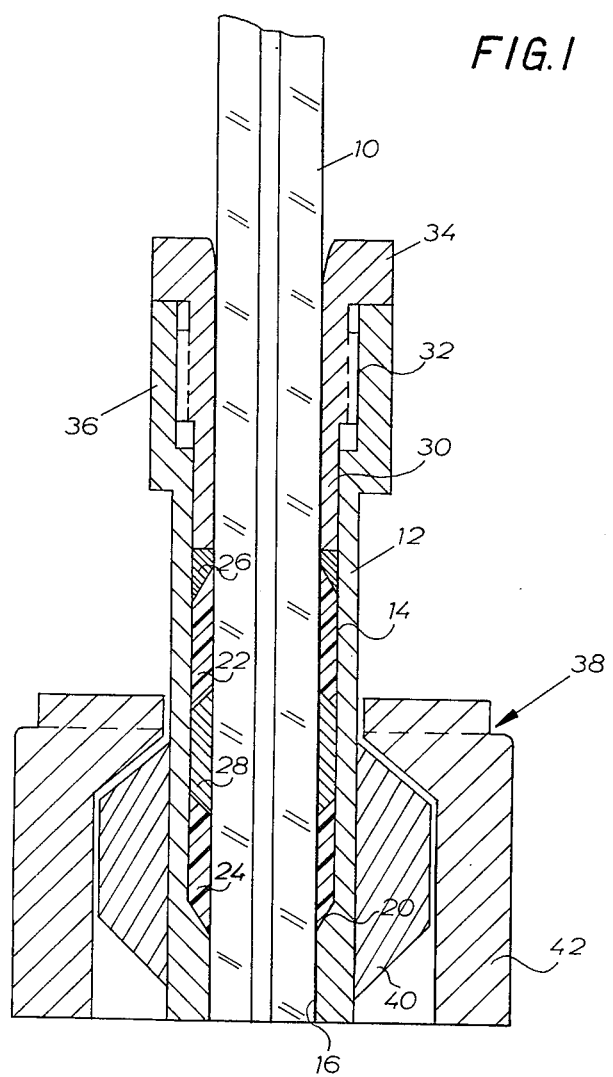

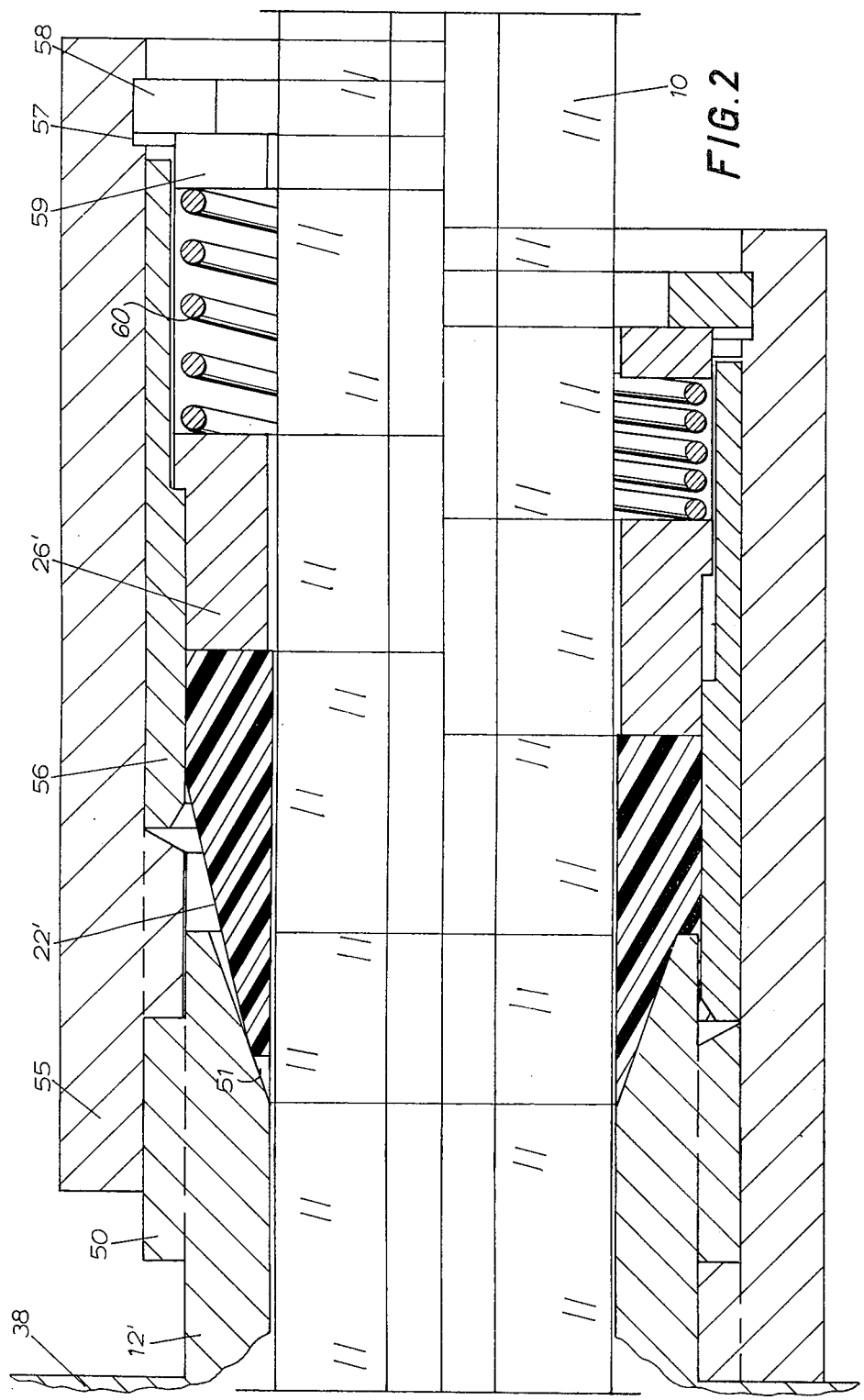

ns and thus a correspondingly frequent detaching of the connections. The prior art glass column connections are not adapted to meet these requirements.

REUSABLE SEALED COUPLING FOR GLASS TUBES

BACKGROUND AND SUMMARY OF THE INVENTION

This invention relates to a connecting device for connecting chromatographic separating columns of glass to terminal fittings on a chromatographic apparatus.

The published German specification 2,029,738 shows a connection fitting for a laboratory apparatus of glass having a connection socket which is provided with grooves to retain a hose pushed thereon. A threaded bushing is slid on the connection socket and a sealing ring of rubber-like resilient material, such as a piece of rubber hose, is pushed on the connection socket, the sealing ring being deformed thereby to closely engage the connection socket and also to fill the grooves therein. The connection fitting slid thereon is threaded with an internal thread on the external thread of the threaded bushing, and the sealing ring is deformed between the connection fitting and the threaded bushing by tightening the thread and is tensioned against the connection socket. The bore of the connection fitting has an inclined shoulder, and, correspondingly, the bore of the threaded bushing has a flaring inclined shoulder at its end facing the sealing ring. A connection fitting of the type having a sealing ring of rubber-like material is neither intended nor suitable for use at high temperatures, such as 350° C., occurring in gas-chromatographic separating columns, as the material of the sealing ring is not able to withstand these temperatures.

Swiss patent 509,591 shows a closure device for a chromatographic tube in which two sealing rings of rubber-like material are interposed between a plug or core member and the internal wall of the chromatographic tube and a spacer tube is arranged between these sealing rings. The sealing rings have trapeziodal cross sections flaring outwardly, whereby they can be pressed by axial pressure against the internal wall of the tube. This axial pressure is exerted by the annular part of a thrust member the conical end face of which engages a conical end face of one sealing ring. A conical surface of a flange provided on the plug engages a conical end face of the other sealing ring. The thrust member is axially adjustable relative to the core member. As in the case of the aforementioned German specification, this closure device is neither intended nor suitable for use at high temperatures because of the material of the sealing ring.

There are various other connecting devices for gas-tight sealing connection of the ends of separating columns to terminal fittings on the chromatographic apparatus. These are the conventional means for detachably and sealingly connecting tubes, such means comprising conical sealing end faces which are tightened by means of a screw cap. Using such connecting devices with chromatographic columns made of glass encounters problems in practice. The presently available detachable connecting devices for chromatographic separating columns made of glass are adapted for use at temperatures up to 230° C. They may be used for a short time and without rapid temperature variations up to temperatures of 300° C. In recent times, however, gas-chromatography requires glass column connections which remain gas-tight even, if a temperature program up to about 350° C. is used, and which are still easily detachable. It is to be noted that gas-chromatography requires frequent interchanging of the separating columns and thus a correspondingly frequent detaching of the connections. The prior art glass column connections are not adapted to meet these requirements.

It is an object of the invention to provide a connecting device for connecting chromatographic columns of glass to the terminal fittings on the apparatus, said connecting device being easily detachable, gas-tight up to 350° C. and indifferent to thermal shocks.

According to the invention, there is a connecting device for connecting chromatographic separating columns of glass comprising connecting means for effecting gas-tight and detachable connection of the ends of the separating column to terminal fittings on a chromatographic apparatus. The ends of the column of glass are surrounded by a metallic sleeve, a sleeve of synthetic plastic having at least one conical end face being interposed therebetween. The synthetic plastic sleeve is held in sealing engagement with the separating column, on one hand, and with the metal sleeve, on the other hand, by a sleeve-shaped thrust member, which is axially adjustable relative to the metallic sleeve. A radial sealing force is exerted on the synthetic plastic sleeve through its conical end face by an abutting complementary conical surface. The connecting means are provided on the metal sleeve.

According to one aspect of the invention the synthetic plastic sleeve consists of a synthetic plastic material which is of substantially stable shape at least up to a temperature of 350° C. even if subjected to pressure.

The invention is based on the discovery that a sufficient radial sealing force can be achieved by the wedge effect through the conical end faces even with a synthetic plastic material which has no rubber-like characteristics but is of substantially stable shape. Thus a temperature resistant synthetic plastic material such as polyimide can be used and, thereby, such a connecting device is adapted to be used for connecting chromatographic separating columns which are subjected to a temperature program up to 350° C.

There are materials which, though they are of substantially stable shape and have no rubber-like characteristics, tend to flow under the influence of the pressure and of high temperature or are subject to material losses due to evaporation, whereby the axial pressure exerted by the thrust member and causing the sealing force relaxes and the seal becomes leaky. A material of this type is, for example, polytetrafluoroethylene. Due to its other especially advantageous characteristics this type of material cannot always be replaced by other materials.

It is a further object of the invention, to provide a connecting device of the type mentioned hereinbefore in which the sealing synthetic plastic sleeve may be made of a material having a tendency to flow or vaporize under the influence of pressure and temperature, and which, nevertheless, remains gas-tight and permits repeated use of any particular sealing plastic sleeve.

It is a more specific object of the invention to provide a connecting device of the type described hereinbefore, in which the sealing synthetic plastic sleeve is made of polytetrafluoroethylene.

According to another aspect of the invention the plastic sleeve is held at an adjustable minimum axial pressure in sealing engagement with the metal sleeve and the separating column. For this purpose one end face of a sleeve-shaped thrust member engages the adjacent end face of the synthetic plastic sleeve, and a spring compressible by means of an axial adjusting device abuts the other end face of the thrust member.

DESCRIPTION OF THE DRAWINGS

FIG. 1 is a vertical sectional view of a first embodiment of a connecting device of the invention as applied to one end of a chromatographic column made of glass;

FIG. 2 is a vertical sectional view similar to FIG. 1 of a second embodiment of a connecting device of the invention.

DESCRIPTION OF SPECIFIC EMBODIMENTS

Referring to FIG. 1, reference numeral 10 designates a gas-chromatographic separating column made of glass which has its end projecting into a metallic sleeve 12 which surrounds the separating column 10 at a distance. The metallic sleeve 12 has a reduced internal diameter at its end (lowermost in FIG. 1) adjacent the apparatus, said reduced internal diameter being slightly less than the external diameter of the separating column 10. A conical shoulder 20 is thus formed between the section 14 of the greater internal diameter and the section 16 of the reduced internal diameter.

Two synthetic plastic sleeves 22 and 24 are interposed as well as two sleeve-shaped thrust members 26 and 28 between the separating column 10 and the metallic sleeve 12 in the section 14. The plastic sleeves 22 and 24 have a convexly conical end face and a concavely conical end face each. The convexly conical end face of the plastic sleeve 24 abuts the conical shoulder 20. The thrust member 28 has two convexly conical front faces of which one abuts the concavely conical front face of the plastic sleeve 24. The other convexly conical front face abuts the concavely conical front face of the plastic sleeve 22, whereas the thrust member 26 has a concavely conical front face abutting the convexly conical front face of the plastic sleeve 22. With an axial pressure exerted on the thrust member 26, the thrust member 28 and the plastic sleeves 22 and 24, by a wedging action, the plastic sleeve 22 will be pressed at its upper end inwardly against the outer surface of the separating column 10 and at its lower end inwardly against the inner surface of section 14 of sleeve 12. Similarly, the plastic sleeve 24 will be pressed at its upper end outwardly against the inner surface of section 14 of metallic sleeve 12 and at its lower end against the outer surface of the separating column 10. As already mentioned, the plastic sleeves may consist of polyimide.

A polyimide which has proved useful for the purposes of this invention is a polyimide having graphite added commercially available from Du Pont de Nemours, Wilmington (Delaware) under the trade mark Mespel SP 21.

The axial pressure is exerted on thrust member 26 by a thrust sleeve 30 which has its external threads screwed into internal threads 32 of the metallic sleeve 12. The thrust sleeve 30 projects beyond the end of the metallic sleeve 12 and has an hexagonal or other non circular tool-engagable head 34 at its projecting end. The metallic sleeve 12 also has an hexagonal or other non-circular tool-engagable head 36 at its end.

Conventional connecting means 38 for gas-tight and detachable connection of tubes are provided at the lower end of the metallic sleeve 12. These connecting means may, for instance, comprise a sealing body 40 and a retaining nut 42. By these connecting means the separating column can be connected to the terminal fittings of the apparatus without the glass or the sealing means (plastic sleeves 22 or 24) in contact with the glass being subjected to any changing loads.

The torque between the metallic sleeve 12 and the thrust sleeve 30 required to exert the axial thrust on the thrust sleeve should be approximately in the order of magnitude of 10 kp-centimeter. The metal parts may consist of stainless steel.

The connecting device according to this invention can be used in gas-chromatographic apparatus up to an operating temperature of at least 662°F also when using a temperature program. The detachable connection is made by using the connecting means common in gas-chromatographic apparatus, so that no changes in the apparatus are required.

The connecting device according to this invention could possibly also be used for connection of other glass parts, for instance, to connect nozzles consisting of glass or the like for flame ionization detectors.

Another embodiment of this invention is shown in FIG. 2 of the drawings and will now be explained and described.

The left-hand portion of FIG. 2 illustrates the connecting device in the open, i.e. unloaded position and the right-hand portion shows the device in the closed, i.e. loaded position.

In FIG. 2 reference numeral 12' designates a metallic sleeve; glass separating column 10 extends through, sleeve 12' which at one end is secured to or integral with connecting means, generally designated 38. Sleeve 12' has an externally threaded portion 50 adjacent its end remote from the apparatus. Internally, this end of the metallic sleeve 12' has a conical recess 51.

A cap body or adjustment sleeve 55 has internal threads engaging the externally threaded portion 50 of sleeve 12'. The internal threads extend part of the length of cap body 55. Coaxially disposed within adjustment sleeve 55 is an intermediate sleeve 56 extending from a point adjacent the internal threads to a point adjacent a groove 57 disposed near the end of cap body remote from metallic sleeve 12'. A retaining ring 58 is inserted into groove 57 with a slip ring 59 partly abutting the inner surface of this retaining ring. The slip ring 59 has a smaller outer diameter than the retaining ring 58 and its inner diameter is larger than the outer diameter of the separating column 10. The retaining ring 58 and the slip ring 59 together form an abutment for one end of a spring 60 disposed between the intermediate sleeve 56 and the separating column 10; the other end of spring 60 abuts an end face of the thrust member 26'. The spring abutment end of the thrust member 26' has a larger diameter than its remaining portion. The thrust member directly abuts the intermediate sleeve 56 and has an inner diameter larger than the outer diameter of the separating column 10. The thrust member 26' has a plane face at the end remote from the spring abutment, against which a plastic sleeve 22' is directly supported. The outer diameter of plastic sleeve 22' is also large enough that its outer surface contacts the intermediate sleeve 56. The inner diameter of the plastic sleeve 22' is slightly larger than the outer diameter of the separating column 10. At its end the apparatus the plastic sleeve 22' is provided with a conical front face corresponding to the recess 51 on the metallic sleeve 12'.

The adjustment sleeve or cap body 55 can, for example, be hexagonal on its outside. Upon rotation of the cap body on the externally threaded portion 50 of the metallic sleeve 12' in a direction to advance it towards the connecting means 38, the intermediate sleeve 56 and, at the same time, the abutment for the spring 60, namely the slip ring 59 and the retaining ring 58, move in the same direction. Thereby, initially the cone-shaped front face of the plastic sleeve 22' is inserted into the cone-shaped recess 51 on the metallic sleeve 12' and upon further rotation of the cap body 55 is finally pressed into this recess under the pressure of the compressed spring 60. The intermediate sleeve 56 is slidable on the plastic sleeve 22' and on the thrust member 26' so that a sealing enclosure of the plastic sleeve 22' is achieved. The spring 60 may be compressed to an extent that even at an elevated temperature at which the material of the plastic sleeve starts flowing or evaporates to small proportions, a sealing abutment of the plastic sleeve both against the recess 51 in the metallic sleeve 12', against the intermediate sleeve 56, and against the separating column 10 is maintained, since under the influence of the spring 60 the contact pressure is maintained to the extent required for the sealing.

The connecting device hereinbefore described ensures that under the test conditions always the minimum pressure required for sealing is applied to the plastic seal 22'. It further enables an application of the connecting device also in connection with temperature-programmed gas chromatographs wherein a frequent and possibly rapid temperature change between ambient temperature and temperatures of above 482°F occurs. The connecting device is repeatedly reuseable, and after a temperature change no exchange of a "used-up" plastic sleeve 22' for a new plastic sleeve is required.

I claim:

1. A connecting device for coupling glass chromatographic separating columns to chromatographic instruments comprising:
   a. a metallic sleeve surrounding an end of such a column;
   b. a sleeve of synthetic plastic material, possessing dimensional stability at temperatures of up to at least 350°C, coaxially interposed between said metallic sleeve and the column, said plastic and metallic sleeves having generally complementary conical end surfaces in confronting relation;
   c. a sleeve-shaped thrust member coaxially disposed about said column and axially displaceable relative to said metallic sleeve;
   d. a second plastic sleeve interposed between said metallic sleeve and the column and axially spaced from said first plastic sleeve, each of said sleeves having a convexly conical surface at one end and a concavely conical surface at the other, said thrust member being disposed axially between said plastic sleeves and having respective conical end surfaces complementary to the proximal ends of the plastic sleeves;
   e. a second thrust member coaxially interposed between the column and said metallic sleeve and having a conical surface complementary to and in confronting relation with the end of the plastic sleeve farthest from the column end;
   f. a thrust sleeve coaxially, slidably disposed about the column and having an end portion slidably received in the metallic sleeve and abutting said second thrust member;
   g. complementary threads on said metallic sleeve and thrust sleeve coacting to enable threaded axial displacement of said thrust sleeve relative to said metallic sleeve thereby generating a radial sealing force between the plastic sleeve, the column, and the metallic sleeve by abutting coation of said complementary end surfaces; and
   h. connection means for detachably coupling said metallic sleeve in gas-tight relation to terminal fittings of a chromatographic instrument.

2. A connecting device according to claim 1 wherein the thrust sleeve projects beyond the end of the metallic sleeve and has a tool-engagable non-circular head at its projecting end.

3. A connecting device according to claim 2 wherein said metallic sleeve also has a tool-engagable non-circular head at its end.

4. A connecting device according to claim 3 wherein the plastic sleeves are fabricated of polyimide.

* * * * *